Aug. 12, 1941. W. KORDES Plant Pat. 484
ROSE PLANT
Filed March 28, 1941
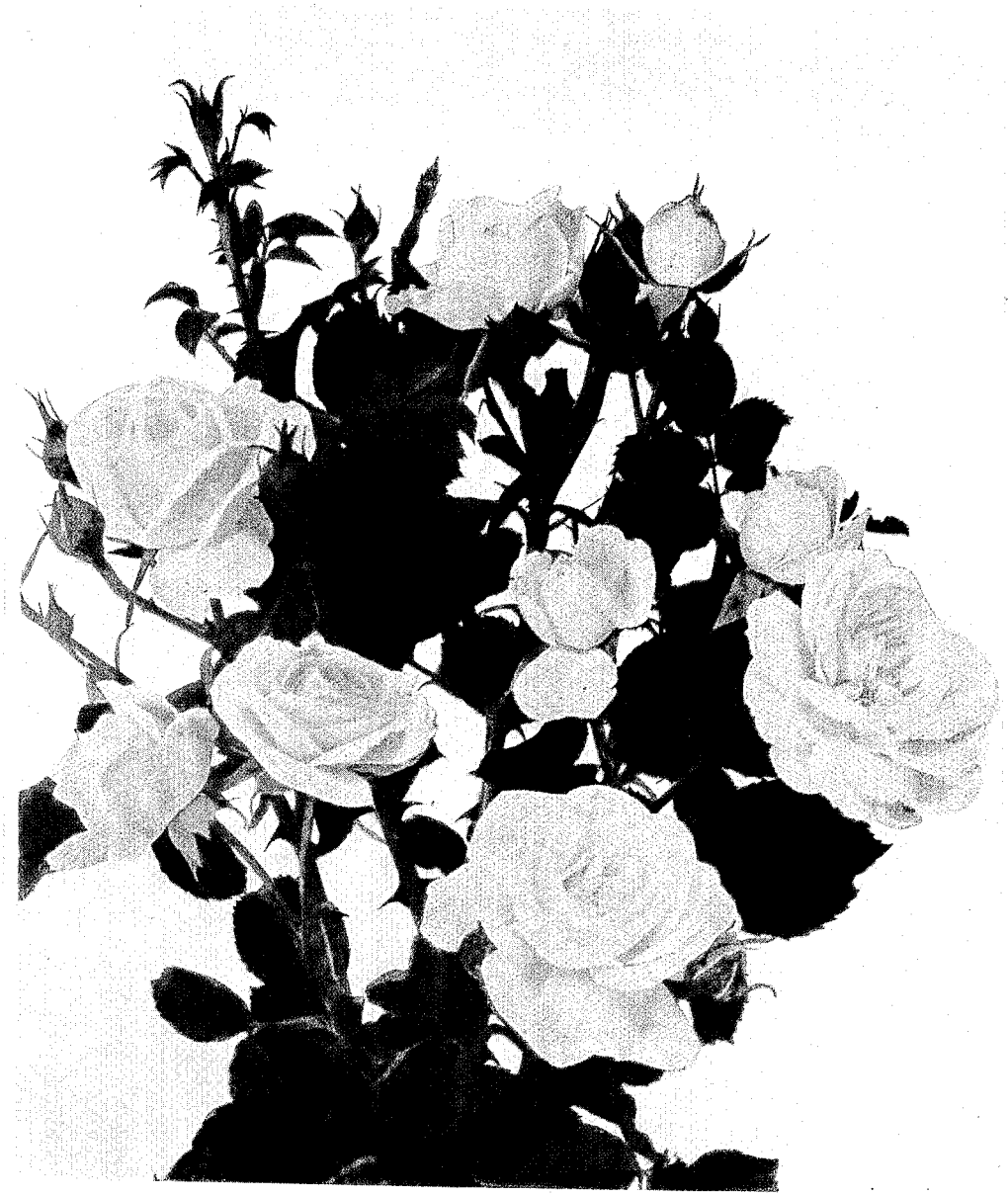
INVENTOR
Wilhelm Kordes
By Robert Cobb
ATTORNEYS.

Patented Aug. 12, 1941

UNITED STATES PATENT OFFICE

484

ROSE PLANT

Wilhelm Kordes, Sparrieshoop in Holstein, Germany, assignor to Jackson & Perkins Company, Newark, N. Y.

Application March 28, 1941, Serial No. 385,762

1 Claim. (Cl. 47—61)

The present invention relates to a new and distinct variety of rose plant in the hybrid polyantha class. This new plant originated from the deliberate crossing of the two well known varieties "Eva" and "Geheimrat Duisberg" which were introduced into the United States a number of years ago, and each of which possessed certain notable characteristics that were desired to be improved by their combination.

The result of the crossing, found in the instant seedling, is primarily distinguished by the new color, in hybrid polyanthas, of the blossoms—Geranium Pink suffused with Apricot Yellow.

Among its other features of novelty may be noted the habit of continuous blooming throughout the summer season; the double petalage averaging thirty to thirty-five petals which drop off cleanly; the very rare Wild Rose fragrance for this class of rose and the firm and disease resistant foliage; all as hereinafter more specifically referred to in the following detail description (color terms being in accord with Ridgway's standard).

Parentage: Seedling.

*Seed parent.*—Eva.

*Pollen Parent.*—Geheimrat Duisberg.

Classification:

*Botanic.*—Polyantha.

*Commercial.*—Floribunda.

*Flower*

Blooming habit: (Observations made in fields and gardens of Jackson & Perkins Company, Newark, New York, in the morning of September 16, 1940.)

*Recurrent—continuous.*

Bud:

*Size.*—Small.

*Form.*—Short and ovoid. Is not affected by wet or hot weather.

*Color.*—When sepals first divide—Spinel Pink, Plate 26, to Light Jasper Red, Plate 13. When petals begin to unfurl—Rose Doree, Plate 1, with Apricot Yellow, Plate 4, blending in at the base. When half blown: inside of petals—Geranium Pink, Plate 1, with a suffusion of Apricot Orange, Plate 14; reverse of petals—between Strawberry Pink, Plate 1, and Geranium Pink, Plate 1, with top edges of Geranium Pink, Plate 1.

*Sepals.*—Slight "hood" above bud. Curl back when petals begin to unfurl.

*Calyx.—Shape*—funnel with long top. *Size*—small; slender. *Aspect*—smooth. *Odor when rubbed*—none.

*Peduncle.—Length*—long. *Aspect*—rough. *Color*—Biscay Green, Plate 17. *Strength*—stiff; slender.

*Opening*: Bud opens well. Is not affected by adverse conditions.

Bloom:

*Size.*—Medium. Average size when fully expanded—2½ inches.

*Borne.*—In clusters, irregular.

*Stems.*—Medium length; strong.

*Form.—When first open*—cupped. *Permanence*—outer petals curl back.

*Petalage.*—Double (full but open center). Number of petals under normal conditions—30–35.

*Color.*—Center of flower—Geranium Pink, Plate 1, showing a cast of Light Orange Yellow, Plate 3, from the base. Outer petals—Geranium Pink, Plate 1. Base of petals (aiglet)—Light Orange Yellow, Plate 3. Inside of petals—Geranium Pink, Plate 1, showing a cast of Light Orange Yellow, Plate 3, from the base. Reverse of petals—between Geranium Pink, Plate 1, and Deep Rose Pink, Plate 12. General tonality from a distance—Geranium Pink, Plate 1.

*Discoloration.*—General tonality at end of first day—Geranium Pink, Plate 1. Second day—Eosine Pink, Plate 1. Third day—Grenadine Pink, Plate 2.

Petals:

*Texture*—Thick. Is not affected by wet or hot weather.

*Appearance.*—Inside—velvety. Outside—shiny.

*Form.*—Oval; notched.

*Arrangement.*—Imbricated (regularly arranged shinglelike). *Petaloids in center*—few; small.

*Persistence.*—Drop off cleanly.

*Fragrance.*—Moderate. *Nature*—wild rose.

*Lasting quality.*—On the plant and as cut flower—long.

Genital organs:

*Stamens, anthers.—Size*—medium; many. *Color*—Light Cadmium, Plate 4. *Arrangement*—regular around styles.

*Stamens, filaments (threads).*—Medium length. *Color*—Empire Yellow, Plate 4.

*Pollen.*—Pinard Yellow, Plate 4.

*Styles.*—Bunched, even; long; thin.

*Stigmas.*—Martius Yellow, Plate 4.

*Ovaries.*—All enclosed in calyx.

*Plant*

Form: Shrub.
Growth: Vigorous; compact.
Foliage: 5–7 leaflets.
*Size.*—Medium.
*Quantity.*—Abundant.
*Color.*—*New foliage:* upper side—Pompeian Red, Plate 13; under side—Acajou Red, Plate 13, with mid-rib and veins of Casse Green, Plate 5. *Old foliage:* upper side—Yew Green, Plate 31; under side—Light Cress Green, Plate 31.
*Shape.*—Oval pointed.
*Texture.*—Upper side—smooth. Under side—rough. *Ribs and veins*—prominent.
*Edge.*—Serrated (saw toothed).
*Serration.*—Single; sharp.
*Rachis.*—*Color*—Light Cress Green, Plate 31. Under side—prickles.
*Stipules.*—Medium length; bearded.
*Disease resistance.*—Resistant.

Wood:
*New wood.*—*Color*—Light Cress Green, Plate 31. *Bark*—smooth.
*Old wood.*—*Color*—Yew Green, Plate 31. *Bark*—Smooth.

Thorns (thorns are divided into thorns, prickles, and short needles):
*Thorns.*—*Quantity*—on main stalks from base and on laterals from stalk—ordinary. *Form*—broad base; medium length; hooked downward. *Color when young*—Acajou Red, Plate 13. *Position*—irregular.

I claim:

A new and distinct variety of hybrid polyantha rose plant, characterized as to novelty by its habit of continuous blooming throughout the summer season, the firm and disease resistant foliage, the unusual color of its flowers and the double petalage thereof, together with the very rare wild rose fragrance of the blooms, substantially as shown and described.

WILHELM KORDES.